United States Patent
Shirley et al.

(10) Patent No.: US 10,950,052 B1
(45) Date of Patent: Mar. 16, 2021

(54) COMPUTER IMPLEMENTED DISPLAY SYSTEM RESPONSIVE TO A DETECTED MOOD OF A PERSON

(71) Applicant: Purity LLC, Salt Lake City, UT (US)

(72) Inventors: Peter Schuyler Shirley, Salt Lake City, UT (US); Jessica E. Johnson, Salt Lake City, UT (US)

(*) Notice: Subject to any disclaimer, the term of this patent is extended or adjusted under 35 U.S.C. 154(b) by 0 days.

(21) Appl. No.: 15/688,552

(22) Filed: Aug. 28, 2017

Related U.S. Application Data

(60) Provisional application No. 62/285,036, filed on Oct. 14, 2016.

(51) Int. Cl.
 *G06T 19/00* (2011.01)
 *G02B 27/00* (2006.01)
 *A61N 5/06* (2006.01)

(52) U.S. Cl.
 CPC .............. *G06T 19/006* (2013.01); *A61N 5/06* (2013.01); *G02B 27/0093* (2013.01); *A61N 2005/0657* (2013.01); *G06T 2207/10004* (2013.01)

(58) Field of Classification Search
 CPC ................... G06T 19/006; G06T 11/60; G06T 2207/10004; G06Q 30/0269; G02B 27/0093; A61N 5/06; A61N 2005/0657
 See application file for complete search history.

(56) References Cited

U.S. PATENT DOCUMENTS

| | | | |
|---|---|---|---|
| 7,415,417 B2 | 8/2008 | Boyer et al. | |
| 8,154,615 B2 | 4/2012 | Fedorovskaya | |
| 8,764,656 B2 | 7/2014 | Shin et al. | |
| 9,292,092 B2 | 3/2016 | Yuxin et al. | |
| 9,313,318 B2 | 4/2016 | Jonsson et al. | |
| 9,400,564 B2 | 7/2016 | Chou et al. | |
| 2002/0097978 A1 | 7/2002 | Lowry et al. | |
| 2009/0207604 A1 | 8/2009 | Robotham | |
| 2011/0141011 A1 | 6/2011 | Lashina et al. | |
| 2014/0309868 A1 | 10/2014 | Ricci | |
| 2015/0029087 A1* | 1/2015 | Klappert | G06F 3/015 345/156 |
| 2015/0113563 A1* | 4/2015 | Woods | H04N 5/765 725/34 |

(Continued)

FOREIGN PATENT DOCUMENTS

| | | |
|---|---|---|
| CN | 104777910 | 7/2015 |
| CN | 105700682 | 6/2016 |
| WO | 2008007293 | 1/2008 |

OTHER PUBLICATIONS

U.S. Appl. No. 62/285,036, filed Oct. 14, 2016, Shirley et al.

(Continued)

*Primary Examiner* — Jeffery A Brier
(74) *Attorney, Agent, or Firm* — Alpine IP PLLC

(57) ABSTRACT

Disclosed are systems and methods for influencing the mood of a person using a synthetic window. The system includes storing one or more excitement scenes and one or more calming scenes, where the excitement scenes when displayed on the display produce an excitatory environment and the calming scenes when displayed on the display produce a calming environment. The system also includes receiving input as to a type of mood of the person, selecting an excitement scene or a calming scene in response to the mood type received, and displaying the selected scene on the display.

20 Claims, 4 Drawing Sheets

(56) References Cited

U.S. PATENT DOCUMENTS

| | | | |
|---|---|---|---|
| 2015/0179015 A1* | 6/2015 | Chang | G07F 9/023 |
| | | | 700/232 |
| 2016/0217322 A1 | 7/2016 | Kim et al. | |
| 2016/0255162 A1* | 9/2016 | Frieder | H04L 67/22 |
| | | | 709/204 |
| 2018/0025219 A1* | 1/2018 | Baldwin | H04L 51/20 |
| | | | 382/118 |
| 2018/0063064 A1* | 3/2018 | Borse | H04L 51/32 |
| 2018/0364649 A1* | 12/2018 | Kim | G04G 9/0064 |

OTHER PUBLICATIONS

"Intel's emotion sensing cameras" http://retail-innovation.com/intels-emotion-sensing-cameras/ (Aug. 15, 2016).
"Emotion tracking in store" http://retail-innovation.com/emotion-tracking-in-store/ (Aug. 15, 2016).
"Japanese digital vending with facial recognition" http://retail-innovation.com/japanese-digital-vending-with-facial-recognition/ (Aug. 15, 2016).

* cited by examiner

COMPUTER IMPLEMENTED DISPLAY SYSTEM RESPONSIVE TO A DETECTED MOOD OF A PERSON

CROSS REFERENCE TO RELATED APPLICATIONS

This application claims the benefit of U.S. Provisional Patent Application No. 62/285,036, filed on Oct. 14, 2016, and titled "Using a Synthetic Window to React to and Adjust a User's Mood," the entire contents of which are hereby incorporated herein by reference.

BACKGROUND

Field of the Invention

The present invention relates to a computer-implemented system that detects a person's mood and changes the state of a display to promote a change in a person's mood from the detected mood to a preselected and/or more preferred mood.

Related Art

A person's mood can be affected by lighting, color, sound, and/or imagery. Light, for example, is known to affect the regulation of emotions, likely through its effects to the nervous and endocrine systems. Lighting, color, sound, and imagery can affect a person's circadian rhythms, influencing physiological parameters such as melatonin levels, serotonin levels, cortical activity, and alertness. In some circumstances, poor lighting, along with a lack of associated color, sound, and imagery can trigger depression and even have a negative effect on the immune system. In contrast, excessive lighting, color, sound, and imagery can cause a person to feel nervous and on edge.

Physical windows, and the associated positive psychological effect they have, are important enough that they often dictate the shape and design of an interior space. Not all interior spaces can accommodate windows, however. Some rooms may be too small and/or located too far toward the interior of a building, for example. In some circumstances, building design may favor less windows to reduce heating or air conditioning costs. A high dynamic range video monitor and speakers can mimic a window by displaying imagery and sound a user might see out a window. Such synthetic windows, when placed on an interior wall, can give the illusion of a window to the outside world.

BRIEF SUMMARY

The present disclosure relates to a display system for influencing the mood of a person. The system includes a display and one or more processors, computer memory, and computer executable instructions stored on a non-transitory recording medium. The execution of the computer executable instructions by the one or more processors causes performance of a method that includes: (i) storing one or more excitement scenes and one or more calming scenes, wherein the excitement scenes when displayed on the display produce an excitatory environment and the calming scenes when displayed on the display produce a calming environment; (ii) receiving mood input and determining a type of mood of the person; (iii) selecting an excitement scene or a calming scene in response to the mood type received; and (iv) displaying the selected scene on the display.

The sound and imagery and resulting lighting from a synthetic window may be adjusted to promote a change in a user's mood. For example, the display may be adjusted in response to detecting a sad person to promote a happier mood, the display may be adjusted in response to detecting a bored person to promote a more engaged and/or excited mood, the display may be adjusted in response to detecting an anxious person to promote a calmer mood, and the like.

To accomplish this the mood of the user is detected. A variety of approaches for detecting user mood may be utilized. In one embodiment, the user may provide input to the system, either verbally and/or through a user interface that receives the type of mood the person is in (e.g., via a touch screen interface and/or microphone with optional voice recognition). Alternatively, or in addition, the system may detect the user's face, and then read the user's expression. Examples of systems that can be adapted to detect mood according to the teachings of the present invention are described in U.S. Pat. No. 8,154,615 to Fedorovskaya and U.S. Pat. No. 9,313,318 to Jonsson, which are incorporated herein by reference.

In some embodiments, the system may use historical data about the individual from previous encounters with the system. In addition, or alternatively, the system may use historical data based on calendar content (e.g., time of year, weekday vs. weekend, workday vs. day off, holiday) and/or time of day. Historical data can be received from a variety of sources. In some embodiments, the system may receive data associated with one or more of a user's eating history, sleep data, movement/exercise history, media consumption (e.g., news, entertainment) history, and the like.

For example, in some embodiments the system may be networked with or otherwise in communication with one or more of a user's other electronic devices and/or applications in order to communicate such historical data. In some embodiments, the system may be configured to communicate with one or more of a user's mobile phone, smart watch, activity tracker, computing device (e.g., work, home, laptop), smart refrigerator, web application, smart television, etcetera.

In some embodiments, the display may be a synthetic (i.e., virtual) window. The synthetic window may be configured to provide imagery (including lighting/brightness levels) and/or sound to provide a display scene mimicking a natural outdoor environment. In some embodiments, for example, the display scene includes a natural landscape. In some embodiments, the landscape includes imagery of a real-life landscape. In some embodiments, the display scene includes moving people, animals, and/or objects within the scene.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

BRIEF DESCRIPTION OF THE DRAWINGS

In order to describe various features and concepts of the present disclosure, a more particular description of certain subject matter will be rendered by reference to specific embodiments which are illustrated in the appended drawings. Understanding that these figures depict just some example embodiments and are not to be considered to be limiting in scope, various embodiments will be described and explained with additional specificity and detail through the use of the accompanying drawings in which.

DETAILED DESCRIPTION

The present disclosure relates to a display system for influencing the mood of a person. The system includes a display and one or more processors, computer memory, and computer executable instructions stored on a non-transitory recording medium. The execution of the computer executable instructions by the one or more processors causes performance of a method that includes: (i) storing one or more excitement scenes and one or more calming scenes, wherein the excitement scenes when displayed on the display produce an excitatory environment and the calming scenes when displayed on the display produce a calming environment; (ii) receiving mood input and determining a type of mood of the person; (iii) selecting an excitement scene or a calming scene in response to the mood type received; and (iv) displaying the selected scene on the display.

Some embodiments further include storing one or more sub-categories of excitement scenes, such as one or more scenes for promoting alertness, one or more scenes for promoting a person to awake from sleep, one or more scenes for promoting user motion/activity, and the like.

Some embodiments further include storing one or more sub-categories of calming scenes, such as one or more scenes for promoting sleep, one or more scenes for dissipating anger, one or more scenes for relieving anxiety, and the like.

Figure 1:
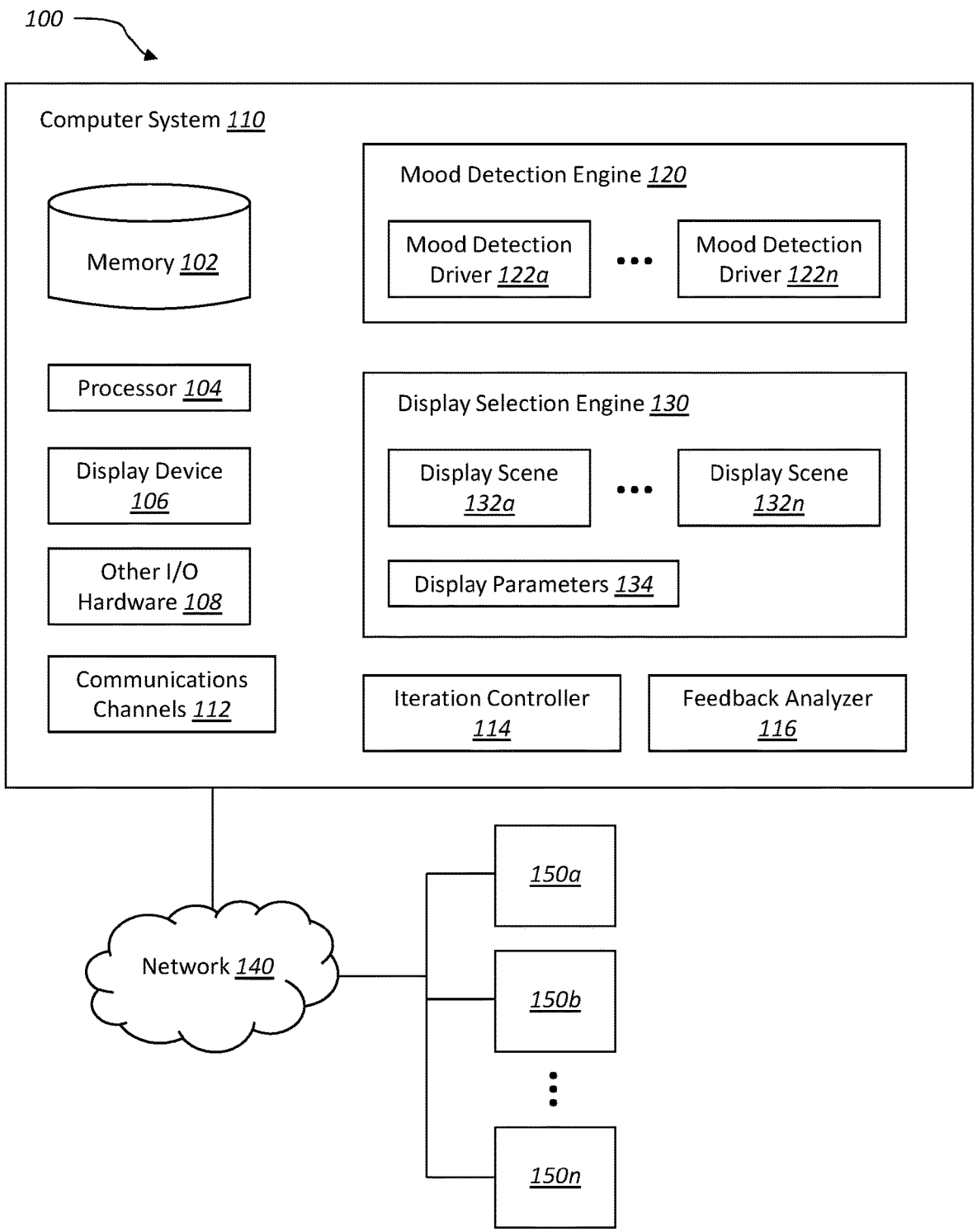
FIG. 1 illustrates a computer system configured for modulating a display for promoting a desired mood change in a person.

FIG. 1 illustrates an exemplary computer environment 100 configured for modulating a display to promote a desired mood change in a person within visual proximity to the display. The illustrated computer environment 100 includes a computer system 110 with a memory 102 and at least one processor 104. Alternative embodiments may include a plurality of processors and/or memory storage devices. The memory 102 may be physical system memory, which may be volatile, non-volatile, or some combination of the two. The term "memory" may also be used herein to refer to non-volatile mass storage such as physical storage media.

The computer system 110 also includes executable modules or executable components, described in more detail below. As used herein, the term "executable module" or "executable component" can refer to software objects, routings, or methods that may be executed on the computing system. The different components, modules, engines, and services described herein may be implemented as objects or processes that execute on the computing system.

The computer system 110 also includes a display device 106. The display device 106 may be physically coupled to the processor 104 and memory 102, or may be physically separated but communicatively linked (e.g., via a direct wired connection or via a wireless connection) to the processor 104 and memory 102. The display device is preferably a high dynamic range video ("HDR") monitor/screen, such as one that is certified HDR by the UHD Alliance according to their standards in place in February of 2017. For purposes of this invention HDR includes at least 60 pixels/degree, 0.0005-540 nits, 90% of the P3 color gambit, and 10 bit depth. Alternatively, other types of display devices may be utilized, including those having a sub-HDR rating or those which may be developed in the future having higher ratings. Although one display device 106 is shown in the Figure, it will be understood that more than one display device may also be utilized.

The computer system 110 can also include other input/output hardware 108, including one or more cameras, keyboards, mouse controls, touch screens, microphones, speakers, display screens, track balls, scroll wheels, biometric sensors (e.g., electroencephalography sensors (EEG), heart rate monitors, eye tracking devices, user temperature sensors), and the like to enable the receiving of information from a user and for displaying or otherwise communicating information to a user.

The illustrated computer system 110 also includes communication channels 112 that enable the computer system 110 to communicate with one or more separate computer systems. For example, the computer system 110 may be a part of network 140, which may be configured as a Local Area Network ("LAN"), a Wide Area Network ("WAN"), or the Internet, for example.

In some embodiments, the computer system 110 is communicatively linked to one or more computer systems or computer devices 150a through 150n (referred to collectively as computer devices 150). The one or more computer devices 150 may be connectable to the computer system 110 through a hardwire connection and/or through a wireless connection. In some embodiments, the one or more computer devices 150 can include one or more a user's mobile phone, smart watch, activity tracker, other computing device (e.g., work, home, laptop), smart refrigerator, smart television, and the like. The one or more computer devices 150 can also include user data associated with a web application (e.g., news feed, email, calendar, media streaming) stored at a remote server. As explained in more detail below, the computer system 110 is capable of receiving data from such computer devices 150 to augment the mood detection engine 120 and/or display scene selection engine 130.

The illustrated computer system 110 also includes a mood detection engine 120 configured to detect the mood of one or more persons in visual proximity to the display device 106. Although the following description will typically refer to a singular person or individual, it will be understood that embodiments may also be configured to detect the mood of multiple individuals. For example, where a group of more than one is within visual proximity to the display device 106, the computer system 110 can be configured to detect the mood of some or each of the individuals present. The overall mood of the group can then be determined as an average based on the individuals sampled or on the most frequently detected mood, for example. In some embodiments, the computer system 110 may give greater weight to the moods of the individual(s) of the group who are actively observing the display device 106 or more frequently observe the display device 106 (e.g., by using a camera and facial detection to determine gaze direction).

The mood detection engine 120 can include one or more mood detection drivers 122a to 122n (referred to collectively as mood detection drivers 122) for receiving and configuring mood inputs and providing mood detection functionality. In some embodiments, a mood detection driver 122 may be configured as a manual input driver enabling the receipt of manually input mood information. For example, a user may use any of the input hardware described above to input a present mood into the computer system 110. In one embodiment, a mood detection driver 122 uses voice recognition to receive a voice input through the computer system microphone specifying the present user mood.

In some embodiments, a mood detection driver 122 is configured according to calendar data. For example, the mood detection driver 122 may operate according to time of day (e.g., a user may be more likely to be anxious during morning hours and more likely to be relaxed during evening hours), according to time of week (e.g., a user may be more likely to be anxious during weekdays and more likely to be relaxed on weekends), according to time of year (e.g., a user may be more likely to be depressed during winter months and more likely to be happy during summer months), according to proximity to events marked on the calendar (e.g., a user may be likely to be anxious before a job interview or may be likely to be frustrated/angry after a day filled with multiple meetings), or combinations thereof. In some embodiments, such calendar data is received by communication of the computer system 110 with the user's mobile phone and/or with a user's calendar application.

In some embodiments, a mood detection driver 122 is configured to operate according to received biometric data (e.g., via communication with a health/fitness tracking device and/or suitable application). The mood detection driver 122 may detect a user's recent exercise/activity level, sleep data, body temperature, pulse/heart rate, or combinations thereof, and infer a likely mood based on the biometric data. For example, a user experiencing a higher than normal heart rate may be more likely to be in an anxious mood, and a user experiencing a drop in typical exercise activity and/or experiencing less sleep than normal may be "edgier" and more likely to experience an angry mood.

In some embodiments, a mood detection driver 122 is configured to operate according to facial expression and/or gaze data, such as data received using a camera associated with the computer system 110. The camera may capture imagery of the user's face, and use facial recognition algorithms known in the art to determine a likely mood of the user.

In some embodiments, a mood detection driver 122 is configured to operate according to received media consumption history (e.g., via communication with the user's news feed, video or music streaming application, etc.). The mood detection driver 122 may detect a user's recent media consumption and infer a likely mood based on the received data. For example, a user who has recently watched a war documentary and/or who has recently read a series of negative news articles may be more likely to experience a depressed mood.

In some embodiments, information from one or more mood detection drivers can be associated with information from one or more other mood detection drivers to augment the performance of the mood detection engine 120. For example, information from a calendar-based mood detection driver can be combined with information from a biometric-based mood detection driver to determine that the user typically gets limited sleep during a particular portion of the week, and is therefore likely to experience an angry mood during that portion of the week.

The mood detection engine 120 may also utilize historical data to improve mood detection performance over time. In some embodiments, mood data corrections and/or mood data manually input by the user are utilized to determine correlations between calendar data, biometric, data, media-consumption data, historical data, and likely user moods. The illustrated computer system 110 also includes a feedback analyzer 116 configured to receive user inputs and/or user corrections and to reconfigure settings within the mood detection engine 120 and/or display scene selection engine 130 based on the received feedback to enable training and improved performance.

For example, if a user frequently provides input that he/she experiences a particular mood during a particular time of day, within a particular time period following exercise, according to the amount of political news stories read that day, etc., a corresponding mood detection correlation can be mapped. In this manner, the mood detection engine 120 can "learn" to better detect user mood in the future with less need for manual input or correction. Such adaptive operation can be provided using one or more machine learning algorithms known in the art.

The mood detection engine 120 may be configured to broadly categorize a user's mood as "depressed" (including moods such as sad, tired, bored, and the like) or "excited" (including moods such as angry, anxious, frustrated, and the like). In some embodiments, the mood detection engine 120 further includes a category of "good/neutral" (including moods such as relaxed, happy, calm, and the like). In some embodiments, the mood detection engine 120 is configured to identify the user's mood more granularly according to one or more of the above-specified sub-categories of moods. As described above, user input and other data may be utilized to train the mood detection engine in accurately detecting user mood.

The computer system 110 also includes a display scene selection engine 130 configured to select and adjust, based on the detected mood of the user, a display scene for display on the display device 106. As shown, the display scene selection engine 130 includes a plurality of display scenes 132a to 132n (referred to collectively as display scenes 132). The display scenes 132 may include a variety of different scenes. Preferably, however, the display scenes 132 include outdoor scenes such as landscape scenes, cityscape scenes, and the like, in order for the display device 106 to mimic a real window providing visualization of the outdoors.

The display scene selection engine 130 also includes display parameters 134 that may be adjusted to modulate the display scenes 132. Display parameters 134 may include, for example, brightness levels, color profile (e.g., amount of blue light vs. red light), contrast, animation levels (e.g., amount of animated movement within a scene), and sound levels.

In some embodiments, the display scenes 132 are broadly categorized as excitement scenes or calming scenes. Excitement scenes are characterized by relatively brighter lighting, relatively more movement within the scene, a color profile with relatively more blue light, higher contrast, and/or more sound (e.g., higher volume and/or more frequent). Calming scenes are characterized by relatively dimmer lighting, relatively less movement within the scene, a color profile with relatively less blue light, lower contrast, and/or less sound (e.g., lower volume and/or less frequent).

In some embodiments, display scenes are scored according to each parameter, and the overall score of each particular display scene can be used to categorize the scene as an excitement scene or as a calming scene. In some embodiments, the parameter scores can be weighted (e.g., according to user preferences) such that some parameters carry more weight in determining the excitement or calming nature of the scene. In some embodiments, a neutral category is established with one or more display scenes having parameter values or an overall parameter score intermediate between the excitement category and the calming category. The display scene selection engine 130 may be configured to allow the user to adjust category boundaries according to preferences.

Some display scenes may be essentially always of one particular type, but other scenes may be changeable by varying the associated display parameters 134 of the scene. For example, a landscape scene showing a field may be categorized as an excitement scene when it shows a bright sun, blue sky, and birds moving in the air and chirping, but may transition to a calming scene when the displayed sky dims and reddens (e.g., showing a sunset) and/or animated birds fly and chirp less, for example.

In some embodiments, the display scene selection engine 130 selects a display based on the detected user mood in order to promote a change in the mood of the user. For example, where a user's mood has been detected generally as excited, the display scene selection engine 130 may operate to select a calming-type display scene, and when the user's mood has been detected generally as depressed, the display scene selection engine 130 may operate to select an excitement-type display scene.

In implementations where more granular mood detection is available, correspondingly more granular display scene selection may also be utilized. For example, where a user's mood is detected as being tired but not necessarily bored, an excitement display that focuses particularly on bright light levels and high levels of blue light may be utilized (e.g., light and color parameters may be weighted more heavily), whereas in circumstances where a user's mood is detected as being bored but not necessarily tired, an excitement display that focuses particularly on high movement and sound levels may be utilized (e.g., movement and sound parameters may be weighted more heavily).

In another example, where a user's mood is detected as being anxious but not necessarily angry, a calming display that focuses particularly on minimizing movement and sound may be utilized (e.g., movement and sound parameters are weighted more heavily), whereas in circumstances where a user's mood is detected as being angry but not necessarily anxious, a calming display that focuses primarily on minimizing brightness may be utilized. Individual preferences may differ, and settings may be adjusted by the user and/or may adapt as the feedback analyzer 116 receives training data as described above.

The display scene selection engine 130 may also operate according to data received from the one or more computer devices 150 and/or from input received from the user. For example, where a user's mood is detected as being depressed (e.g., sad, bored, or tired), but time/calendar data indicates that it is late in the evening, the display scene selection engine 130 may temper or forego displaying an excitement scene high in blue light and/or light intensity, which could disrupt the expected upcoming sleep of the user.

In another example, where a user's mood is detected as being excited, but biometric data indicates that the user is exercising, the display scene selection engine 130 may temper or forego displaying a calming scene, as the user may prefer a more excited display state for motivation during the exercise routine.

In some embodiments, the display scene selection engine 130 selects a display scene 132 and/or adjusts display parameters 134 according to the intensity of the detected user mood (e.g., the distance of the "depressed" or "excited" user mood from a "good/neutral" mood category). For example, where user mood is detected as being depressed, and an excitement scene is selected and/or modulated to be relatively bright, the degree of brightness may correspond to the degree of the depressed mood of the user. Brightness may be higher where the user mood is detected as being very depressed than where the user mood is detected as being slightly depressed. Likewise, where user mood is detected as being anxious, a selected calming scene may include dimness, sound levels, motion levels, and/or color profiles that vary according to the degree of detected anxiousness.

In some embodiments, the display scene selection engine 130 also includes a variation control enabling a user to vary the degree of alignment between operation of the display scene selection engine 130 and the mood detection engine 120. For example, the display scene selection engine 130 may be set so as to always provide a display scene that corresponds to the detected user mood. The variation control allows the user to introduce varying levels of divergence from the normal set of displays and/or display parameters corresponding to the detected user mood. The variation control can therefore introduce a desired level of variation that may also aid in the generation of better training data.

The illustrated embodiment also includes an iteration controller 114 configured to iterate mood detection and display scene detection over time. For example, the iteration controller 114 may initiate the mood detection engine 120 to redetect the mood of the user to see if the user mood has changed since the previous measurement. If the resulting measurement requires an adjustment to the display scene, the display scene selection engine 130 may be initiated to operate accordingly.

In one example, if one or more previous display scenes have not resulted in a desired change in user mood (or fast enough change in user mood), the display scene selection engine 130 may ramp up or down display scene parameters (e.g., brightness, color settings, motion activity, sound levels, and/or overall scene selection) until the effect on user mood begins to trend in the desired direction and/or begins to trend at a desired rate. For example, if a user's mood is previously detected as "depressed," and after a period of time the mood is still detected as "depressed," the display scene selection engine 130 may operate to increase brightness, blue light, motion, or sound of the displayed scene, or may operate to change the scene to one having more of at least one of these characteristics.

In some embodiments, after a successful change in user mood has been detected, the display scene selection engine 130 can revert to selecting a default/neutral display scene. For example, when a user's mood is detected as "good/neutral" after being either, for example, "depressed" or "excited," the selected display can be chosen as one having intermediate settings which do not necessarily promote excitement or calming effects.

In some embodiments, memory components and/or program modules are distributed across a plurality of constituent computer systems in a distributed environment. In other embodiments, memory components and program modules are included in a single integrated computer system. Accordingly, the systems and methods described herein are not intended to be limited based on the particular location at which the described components are located and/or at which their functions are performed.

Figure 2A:
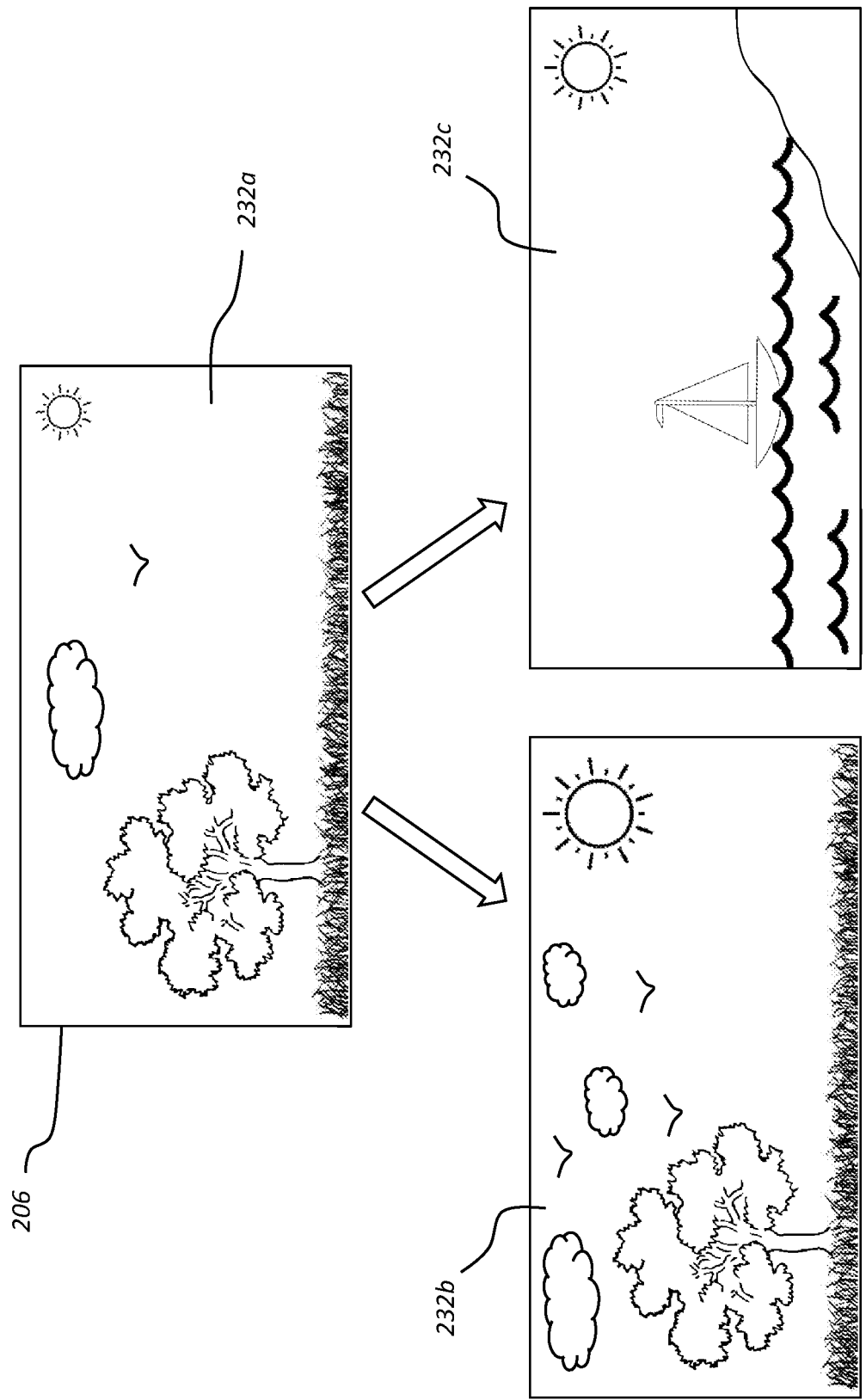
FIGS. 2A and 2B illustrate a display device adjusting a display screen according to exemplary implementations of the computer system of FIG. 1.
Figure 2B:
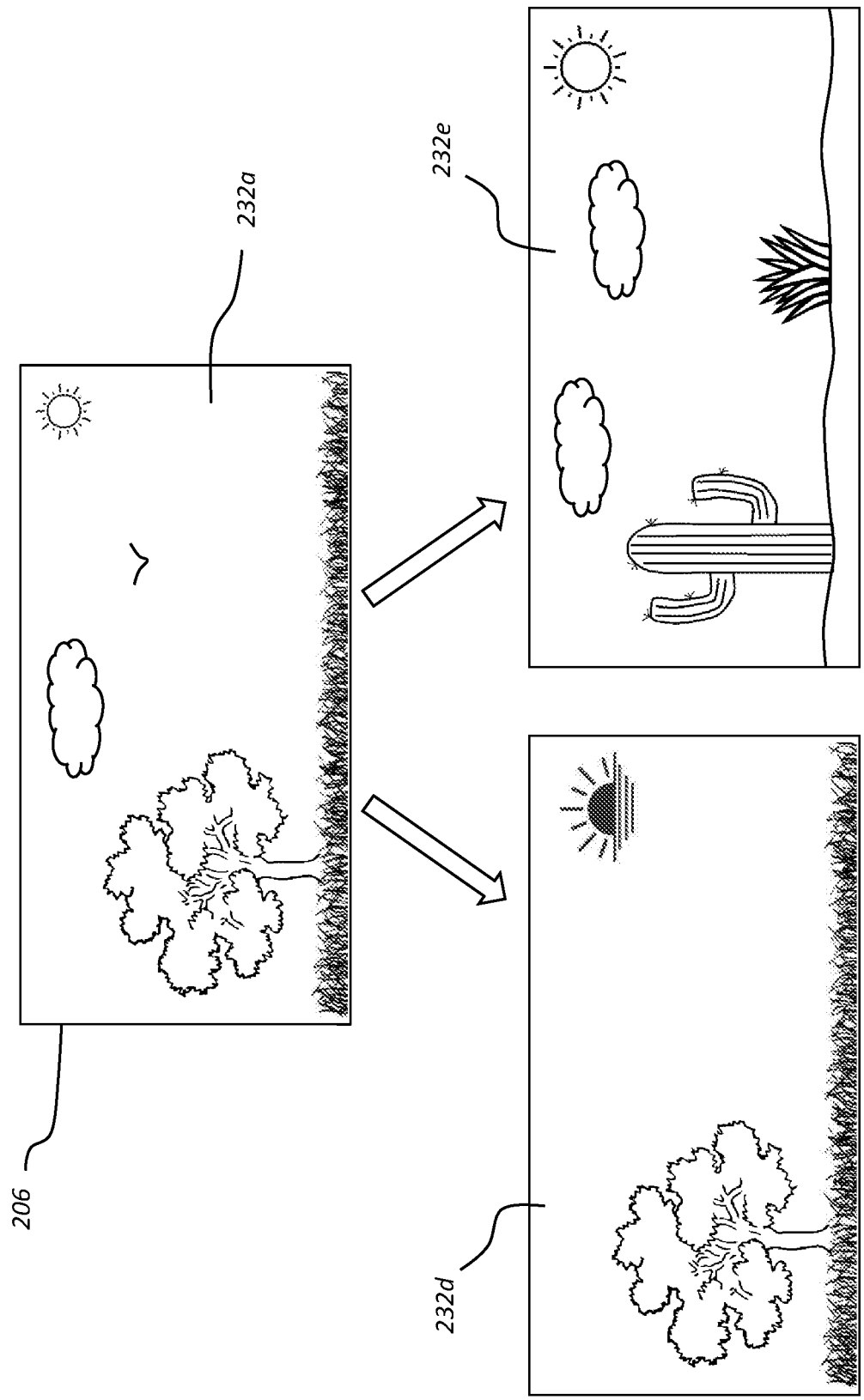

FIGS. 2A and 2B illustrate operation and functionality of various exemplary embodiments for modulating the display of a synthetic window in order to promote a mood change in a person. These exemplary embodiments may be carried out using the computer environment 100 described above.

FIG. 2A illustrates a display device 206 which is at first showing a default display scene 232a. The default display scene 232a may be a neutral scene. In other embodiments, the default display scene may be a slideshow or a randomly selected scene or series of scenes. In some embodiments, the default display scene may simply be the last scene displayed since the most recent change intended to promote a mood change in the user. For example, if the most recent promoted mood change was successful, and no subsequent negative mood has been detected in the user, the scene may continue unchanged until another negative mood is detected.

In the example shown in FIG. 2A, the display scene 232a is a neutral scene. Upon detection of a negative mood in the user, the computer system causes the display 206 to be updated to a modified display scene configured to promote a mood change in the user. In the illustrated example, the user's mood is detected as being "depressed" (e.g., sad, tired, bored). In response, the computer system updates the display scene 232a to an "excitement scene" to promote a less depressed mood in the user. If the present scene is already an excitement scene, the display scene may still be updated to a scene having a higher excitement score.

In one example, the display scene update can be carried out by maintaining the overall environment of the scene, but modifying one or more of the parameters so that the scene becomes more excitatory. As shown by display scene 232b, the overall viewing environment is maintained (e.g., same field, tree, and background), but the sun has been made more prominent to increase brightness, and more clouds and birds have been added to increase motion and sound activity within the scene.

In another example, the display scene can be switched to a new display scene having a new viewing environment. For example, the grassy field display of the display scene 232a may be switched to a display scene 232c showing an oceanfront view. The updated view 232c may have higher blue light content, more brightness, more motion, and/or more sound activity to provide a higher excitement score than the previous display scene 232a.

FIG. 2B shows another example where the same display scene 232a is displayed, but the user's mood is detected as being "excited" (e.g., anxious, angry, frustrated). Upon detecting this mood, the computer system causes the display scene to update to a "calming scene." If the presently displayed scene is already a calming scene, the display may still be updated to a scene having a higher calming score.

In one example, the display scene is updated by maintaining the same overall viewing environment, but modifying one or more parameters to make the scene more calming. As shown by display scene 232d, the overall viewing environment is maintained (e.g., same field, tree, and background), but the sun has been rendered as a sunset to lower brightness, and less clouds and birds are present to reduce motion and sound activity within the scene.

In another example, the display scene can be switched to a new display scene having a new viewing environment. For example, the grassy field display of the display scene 232a may be switched to a display scene 232e showing a desert view. The updated view 232e may have lower blue light content, for example, to provide a higher calming score than the previous display scene 232a.

In the description that follows, embodiments are described with reference to acts that are performed by one or more computing systems. If such acts are implemented in software, one or more processors of the associated computing system that performs the act direct the operation of the computing system in response to the processor(s) of the computing system having executed computer-executable instructions that are embodied on one or more computer-readable media (e.g., hardware storage device(s)).

Figure 3:
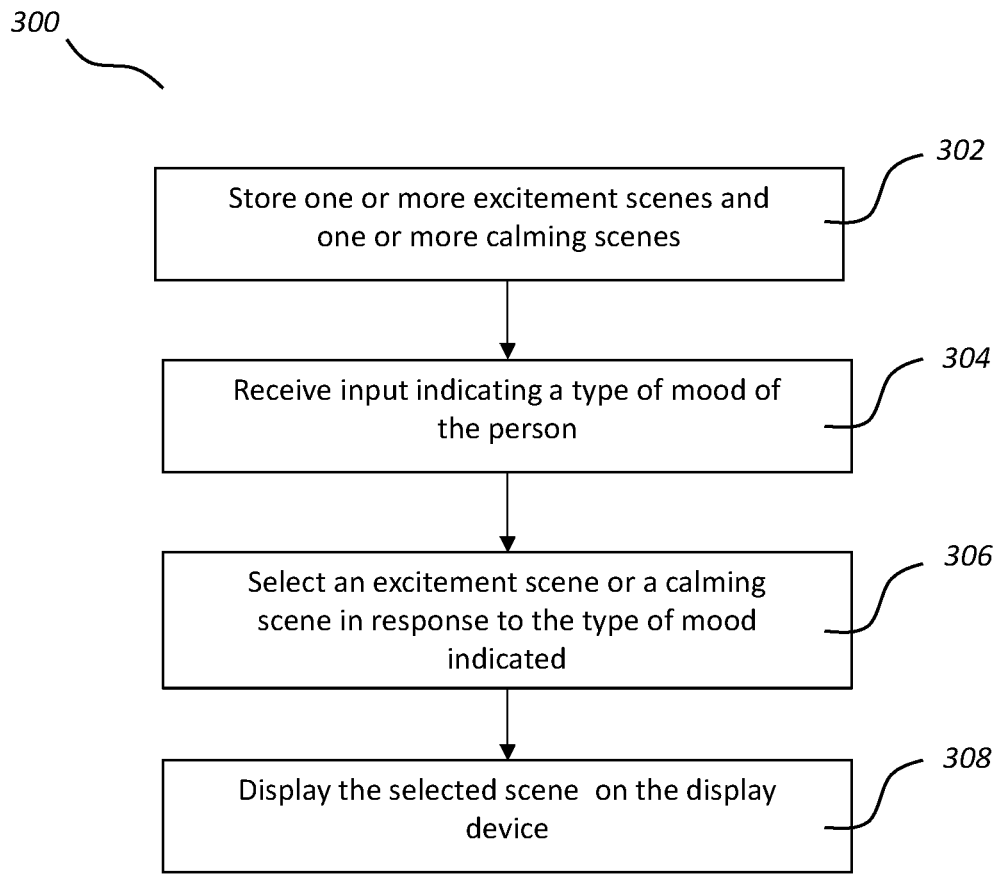
FIG. 3 illustrates a flowchart of an exemplary method, which may be performed using the computer system of FIG. 1, for modulating a display for promoting a desired mood change in a person.

FIG. 3 is a flowchart of a computer-implemented method 300 for modulating a display to promote mood change in a person. As shown, a computer system operates to store one or more excitement scenes and one or more calming scenes (act 302). The one or more excitement scenes are configured to, when displayed on a display device, provide an excitatory environment. The one or more calming scenes are configured to, when displayed on a display device, provide a calming environment.

The computer system then receives input indicating a type of mood of the person (act 304). As described above, mood detection may be accomplished using one or more of facial expression data, calendar/time data, biometric data, user history, and user manual inputs, for example.

The computer system then selects an excitement scene or a calming scene in response to the mood type indicated (act 306), and displays the selected scene on the display device (act 308).

The disclosed embodiments may comprise or utilize a special-purpose or general-purpose computer system that includes computer hardware, such as, for example, one or more processors and system memory. Embodiments within the scope of the present invention also include physical and other computer-readable media for carrying or storing computer-executable instructions and/or data structures. Such computer-readable media can be any available media that can be accessed by a general-purpose or special-purpose computer system. Computer-readable media that store computer-executable instructions and/or data structures are computer storage media. Computer-readable media that carry computer-executable instructions and/or data structures are transmission media. Thus, by way of example, and not limitation, embodiments of the invention can comprise at least two distinctly different kinds of computer-readable media: computer storage media and transmission media.

Computer storage media are physical storage media that store computer-executable instructions and/or data structures. Physical storage media include computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the disclosed functionality of the invention.

Transmission media can include a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be included within the scope of computer-readable media.

Further, upon reaching various computer system components, program code in the form of computer-executable instructions or data structures can be transferred automatically from transmission media to computer storage media (or vice versa). For example, computer-executable instructions or data structures received over a network or data link can be buffered in RAM within a network interface module (e.g., a "NIC"), and then eventually transferred to computer system RAM and/or to less volatile computer storage media at a computer system. Thus, it should be understood that computer storage media can be included in computer system components that also (or even primarily) utilize transmission media.

Computer-executable instructions comprise, for example, instructions and data which, when executed at one or more processors, cause a general-purpose computer system, special-purpose computer system, or special-purpose processing device to perform a certain function or group of functions. Computer-executable instructions may be, for example, binaries, intermediate format instructions such as assembly language, or even source code.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, virtual or augmented reality headsets, and the like. The invention may also be practiced in distributed system environments where local and remote computer systems, which are linked (either by hardwired data links, wireless data links, or by a combination of hardwired and wireless data links) through a network, both perform tasks. As such, in a distributed system environment, a computer system may include a plurality of constituent computer systems. In a distributed system environment, program modules may be located in both local and remote memory storage devices.

Those skilled in the art will also appreciate that the invention may be practiced in a cloud computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

A cloud computing model can be composed of various characteristics, such as on-demand self-service, broad network access, resource pooling, rapid elasticity, measured service, and so forth. A cloud computing model may also come in the form of various service models such as, for example, Software as a Service ("SaaS"), Platform as a Service ("PaaS"), and Infrastructure as a Service ("IaaS"). The cloud computing model may also be deployed using different deployment models such as private cloud, community cloud, public cloud, hybrid cloud, and so forth.

Some embodiments, such as a cloud computing environment, may comprise a system that includes one or more hosts that are each capable of running one or more virtual machines. During operation, virtual machines emulate an operational computing system, supporting an operating system and perhaps one or more other applications as well. In some embodiments, each host includes a hypervisor that emulates virtual resources for the virtual machines using physical resources that are abstracted from view of the virtual machines. The hypervisor also provides proper isolation between the virtual machines. Thus, from the perspective of any given virtual machine, the hypervisor provides the illusion that the virtual machine is interfacing with a physical resource, even though the virtual machine only interfaces with the appearance (e.g., a virtual resource) of a physical resource. Examples of physical resources including processing capacity, memory, disk space, network bandwidth, media drives, and so forth.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A display system responsive to a detected mood of a person, the system including:
   a display device; and
   one or more processors, computer memory, and computer executable instructions stored on a non-transitory recording medium, wherein execution of the computer executable instructions by the one or more processors causes performance of a method comprising:
      storing a set of display scenes configured for display on the display device, each particular display scene having a plurality of excitement parameters that set an excitement level thereof, the plurality of excitement parameters selected from brightness level, color profile, contrast, motion level, sound volume and sound frequency;
      receiving mood input and determining a type of mood of the person using a mood detection engine;
      selecting a display scene from the set of display scenes using at least in part the mood type detected; and
      displaying the selected scene on the display device, thereby responding to the detected mood of the person.

2. The display system as in claim 1, further comprising providing a user interface for indicating the detected mood type from a user and receiving input from a user regarding the mood type.

3. The display system as in claim 2, wherein the user interface is a touch screen interface displaying an input field.

4. The display system as in claim 2, wherein the user interface includes a microphone and voice recognition for receiving user input.

5. The display system as in claim 1, further comprising an imaging system that captures images of the person, wherein the mood input comprises the captured images.

6. The display system as in claim 1, wherein receiving mood input includes receiving calendar data, the method further comprising and determining the type of mood of the person based at least in part on the calendar data.

7. The display system as in claim 1, wherein receiving mood input includes receiving biometric data and determining the type of mood of the person based at least in part on the biometric data.

8. The display system as in claim 1, wherein receiving mood input includes receiving media consumption data associated with the person and determining the type of mood of the person based at least in part on the media consumption data.

9. The display system as in claim 1, wherein at least a portion of the plurality of are unequally weighted.

10. The display system as in claim 1, wherein the selected scene replaces a previous scene, and wherein the selected scene is more excitatory or more calming than the previous scene.

11. The display system as in claim 10, wherein the selected scene and the previous scene maintain the same viewing environment.

12. The display system as in claim 10, wherein the selected scene includes a different viewing environment than the previous scene.

13. The display system as in claim 1, wherein the selected scene is selected according to an intensity of the type of mood of the person, the selected scene having an excitatory score or a calming score corresponding to the intensity of the type of mood of the person.

14. The display system as in claim 1, further comprising detecting the type of mood of the person a second time, and further comprising, in response to detecting that the type of mood of the person a second time, adjusting the selected scene or selecting a new scene such that a newly displayed scene is more excitatory or more calming than the initially selected scene.

15. A display system responsive to a detected mood of a person, the system including:
   a display device; and
   one or more processors, computer memory, and computer executable instructions stored on a non-transitory recording medium, wherein execution of the computer executable instructions by the one or more processors causes performance of a method comprising:
      storing at least one display scene configured for display on the display device, the at least one display scene having a plurality of excitement parameters that set an excitement level of the display scene, the plurality of excitement parameters selected from brightness level, color profile, contrast, motion level, sound volume and sound frequency;
      receiving mood input and determining a type of mood of the person using a mood detection engine;
      selecting a value for each of the plurality of excitement parameters based at least in part on the mood type detected; and
      displaying the at least one scene on the display device using the excitement parameters.

16. The display system as in claim 15, further comprising providing a user interface for indicating the detected mood type from a user and receiving input from a user regarding the mood type.

17. The display system as in claim 16, wherein the user interface is a touch screen interface displaying an input field.

18. The display system as in claim 16, wherein the user interface includes a microphone and voice recognition for receiving user input.

19. The display system as in claim 15, further comprising an imaging system that captures images of the person, wherein the mood input comprises the captured images.

20. The display system as in claim 15, wherein receiving mood input includes receiving calendar data, the method further comprising determining the type of mood of the person based at least in part on the calendar data.

* * * * *